June 10, 1975 W. A. WARRINER Plant Pat. 3,729
ROSE PLANT
Filed April 24, 1974
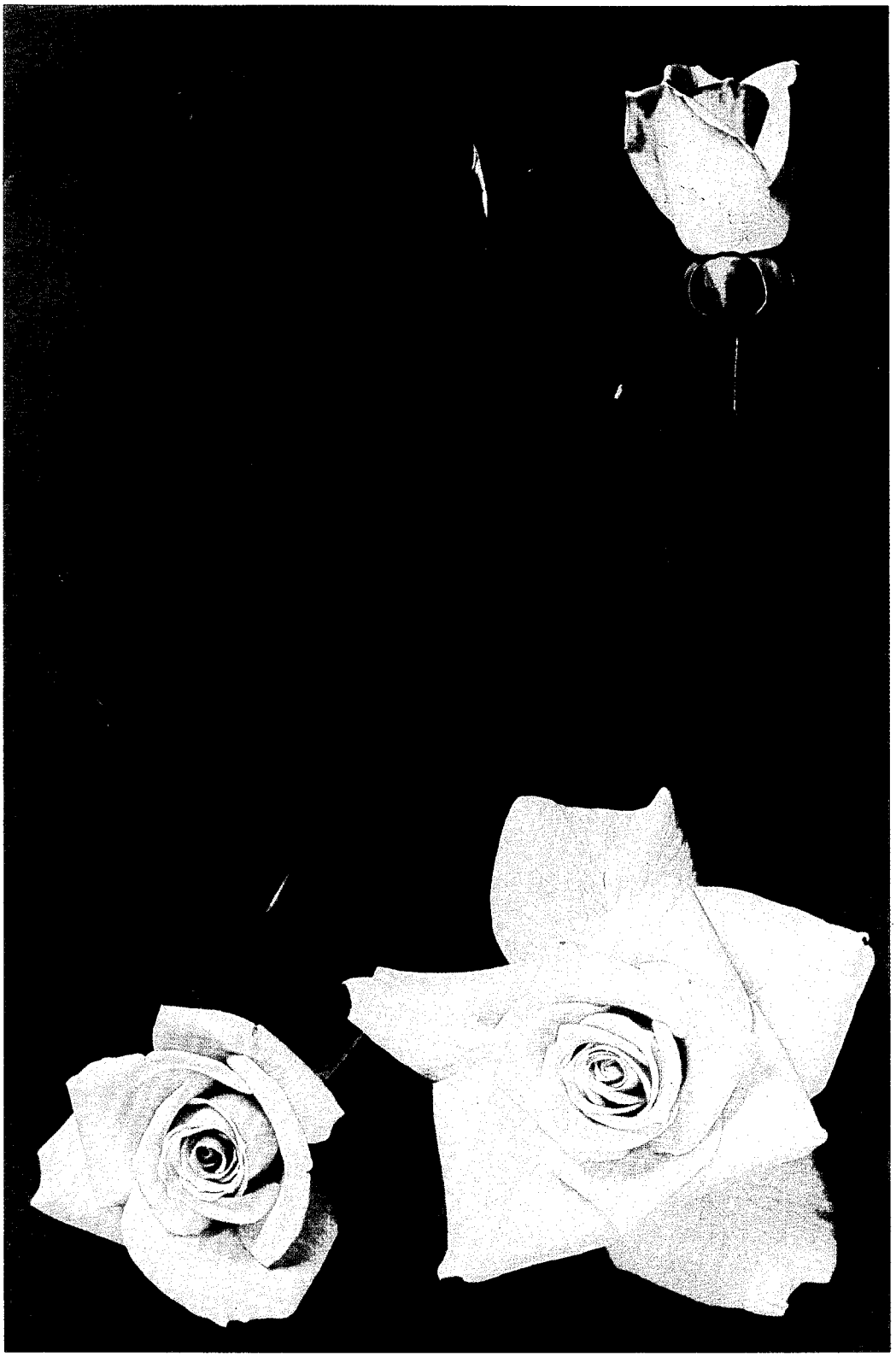

United States Patent

Plant Pat. 3,729

Patented June 10, 1975

3,729

ROSE PLANT

William A. Warriner, Tustin, Calif., assignor to Jackson & Perkins Company, Medford, Oreg.

Filed Apr. 24, 1974, Ser. No. 463,502

Int. Cl. A01h 5/00

U.S. Cl. Plt.—18 1 Claim

The present invention relates to a new and distinct cultivar of rose plant of the hybrid tea class, which was originated by me by crossing the cultivar Bridal Pink, U.S. Plant Pat. No. 2,851, with pollen from an unnamed cultivar.

The primary objective of this breeding was to produce a cultivar particularly suitable for production of cut flowers with a color similar to that of Bridal Pink, but with larger flower buds and blooms and longer stems. This objective was fully achieved as evidenced by the following unique combination of characteristics which are outstanding in the new cultivar and which distinguish it from its parents as well as from all other cultivars of which I am aware:

1. A vigorous habit of growth.
2. Strong, long flower stems suitable for cut flowers, normally longer than those of Bridal Pink when grown in a similar environment.
3. Strong peduncles that remain stiff and erect when used as cut flowers.
4. Flower buds similar in shape and color to Bridal Pink but normally larger when grown in a similar environment.
5. A definite resistance to powdery mildew.

Asexual reproduction of the new cultivar by budding, as performed at Wasco, Calif., shows that the described characteristics and distinctions come true to form and are established and transmitted through succeeding propagations.

The accompanying illustration shows typical specimens of the vegetative growth and flowers of the new cultivar in different stages of development, depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling.

*Seed parent.*—Seedling of Bridal Pink, Plant Pat. No. 2,851.

*Pollen parent.*—Unnamed cultivar.

Classification:

*Botanic.*—Rosa hybrid.

*Commercial.*—Hybrid tea.

FLOWER

Observations were made at Irvine, Calif. in January, from plants in a greenhouse.

Blooming habit: Recurrent-continuous.

Bud:

*Size.*—1½ inches when petals start to unfurl.

*Form.*—Pointed, ovoid.

*Color.*—When sepals first divide—near Camellia Rose (622) on outer portion of petals, becoming lighter toward center of petal to near white in center area. Color slightly mottled. When half blown; upper side of petals mostly Camellia Rose (622/1) with near white area at base of petal; lower side of petals near Camellia Rose (622) on outer portions of petal, becoming lighter toward center of petal to near white in center area.

*Sepals.*—Color: Outer surface—mostly Scheeles Green (860/1), center area near (860/3). Inner surface—mostly Scheeles Green (860/2), center area near (860/3) or lighter. Light covering of white tomentum. Three appendaged sepals lightly appendaged. Two unappendaged sepals slightly hairy edged.

*Receptacle.*—Color: Scheeles Green (860/1). Shape: Funnel. Size: Large, long. Surface: Smooth.

*Peduncle.*—Length: Long. Surface: Nearly smooth, slightly glandular. Color: Scheeles Green (860/1). Strength: Stiff, erect.

*Opening.*—Spiral fashion, petal edges curl back slightly.

Bloom:

*Size.*—Medium. Average open size 4½" to 5".

*Borne.*—Singly, occasionally several together.

*Stems.*—Long.

*Form.*—When first open, high centered. Permanence—outer petal edges slightly curled.

*Petalage.*—Number of petals under normal conditions, 30.

*Color.*—Upper side of petals—French Rose (520/1) with darker veins. Color blends toward base of petal with light yellow becoming near Sulfur Yellow (1/2) at petal base. Reverse side of petals—slightly mottled Carmine Rose (621/1) becoming near white near base of petal. Generally tonality from a distance—French Rose (520/1) with the near white of the petal base very evident. Variegations—darker veins as noted.

*Discoloration.*—General tonality at end of first day—little change. Third day—Color begins to lighten French Rose (520/3) to a slightly lighter color after 4 or 5 days.

*Fragrance.*—Slight.

*Petals.*—Thick.

*Shape.*—Round.

*Form.*—Tips slightly recurved.

*Arrangement.*—Imbricated.

*Petaloids in center.*—Few, small.

*Persistence.*—Drop off cleanly.

*Lastingness.*—On the plant—very long. As cut flower—very long.

Reproductive parts:

*Stamens, anthers.*—Medium, many. Color—yellow. Arrangement—regular around styles.

*Filaments.*—Color—white.

*Pollen.*—Lemon yellow.

*Styles.*—Color—Crimson (22).

*Stigmas.*—Color—white.

PLANT

Form: Bush.

Growth: Vigorous, upright, branching.

Foliage: Number of leaflets on normal mid-stem leaves, 5 or 7.

*Size.*—Large.

*Quantity.*—Normal.

*Color.*—New foliage: Garnet Brown (00918/3). Old foliage: near Parsley Green (00962).

Leaflets:

*Shape.*—Oval pointed to elliptic.

*Texture.*—Upper side—leathery.

*Edge.*—Undulated.

*Serration.*—Single, medium.

*Petiole.*—Rachis—green. Underside—prickles.

*Stipules.*—Medium. Edges slightly glandular.

*Disease resistance.*—Resistant to mildew, under normal growing conditions at Irvine, Calif.

Wood:

*New wood.*—Color—light green, Garnet Brown shadings. Bark—smooth.

*Old wood.*—Color—green. Bark—smooth.

Prickles:

*Quantity.*—On main stalks from base—ordinary. On laterals—ordinary.

*Form.*—Broad based. Long, hooked downwardly.

*Color when young.*—Garnet Brown (00918/3).

*Position.*—Irregular.

Small prickles:

*Quantity.*—On main stalks—few. On laterals—few.

*Color.*—Brown.

I claim:

1. A new and distinct cultivar of rose plant of the hybrid tea class, substantially as herein shown and described, characterized particularly as to novelty by the unique combination of a vigorous habit of growth, relatively larger foliage than the cultivar Bridal Pink, relatively larger buds and blooms than the cultivar Bridal Pink, a high degree of resistance to powdery mildew, long stems suitable for use as cut flowers, a bud and flower color of Camellia Rose opening to French Rose.

No references cited.

ROBERT E. BAGWILL, Primary Examiner